(12) United States Patent
DeToro et al.

(10) Patent No.: US 6,464,659 B1
(45) Date of Patent: Oct. 15, 2002

(54) PRESSURE RELIEF INSERT FOR THERAPEUTIC FOOT ENCLOSURES

(75) Inventors: William DeToro, Poland; Brian Perala, Geneva; Aaron J. Kent, Boardman, all of OH (US)

(73) Assignee: Anatomical Concepts, Inc., Youngstown, OH (US)

( * ) Notice: Subject to any disclaimer, the term of this patent is extended or adjusted under 35 U.S.C. 154(b) by 0 days.

(21) Appl. No.: 09/882,988

(22) Filed: Jun. 18, 2001

(51) Int. Cl.[7] .................................................. A61F 5/00
(52) U.S. Cl. ............................ 602/27; 602/23; 602/66
(58) Field of Search ............................ 602/27–29, 23, 602/66; 128/882; 36/7.5, 7.6, 7.7, 7.1

(56) References Cited

U.S. PATENT DOCUMENTS

| | | | | |
|---|---|---|---|---|
| 3,814,088 A | * | 6/1974 | Raymond | 602/27 |
| 4,597,196 A | * | 7/1986 | Brown | 36/44 |
| 4,785,557 A | * | 11/1988 | Kelley et al. | 36/32 R |
| 5,329,705 A | | 7/1994 | Grim et al. | |
| 5,545,127 A | * | 8/1996 | DeToro | 602/27 |
| 5,593,383 A | * | 1/1997 | DeToro | 602/27 |
| 5,762,622 A | | 6/1998 | Lamont | |
| 5,908,398 A | * | 6/1999 | DeToro | 602/16 |
| 6,090,059 A | * | 7/2000 | Wasserman et al. | 602/27 |

* cited by examiner

Primary Examiner—Michael A. Brown
Assistant Examiner—Lalita M. Hamilton
(74) Attorney, Agent, or Firm—Harpman & Harpman

(57) ABSTRACT

A heel and forefoot plantar surface suspension device to be located to relieve pressure to ulcerated or injured forefoot and heel areas of a patient's foot. A contoured elongated pad of synthetic resin foam that has specific qualities of high-density shapeability characteristics is positioned on the foot engagement portion of the therapeutic foot enclosure that will selectively isolate and suspend alternately the plantar forefoot portion or plantar heel portion from direct contact engagement with opposing engagement surfaces.

11 Claims, 5 Drawing Sheets

PRESSURE RELIEF INSERT FOR THERAPEUTIC FOOT ENCLOSURES

BACKGROUND OF THE INVENTION

1. Technical Field

This device relates to footgear having orthopedic soles providing pressure relief to selective areas of the foot.

2. Description of Prior Art

Prior art devices of this type have relied on a variety of different foot cushions to aid in the distribution on weight and thus pressure relief to injured areas of the foot. Such devices are typified by insole inserts of cushion material or synthetic resin foam pads with removable areas to isolate specific portions of the foot for non-contact. See for example U.S. Pat. Nos. 5,329,705, 5,762,622.

In U.S. Pat. No. 5,329,705 a foot gear with pressure relief zone is disclosed in which an inner sole has a plurality of removable sections that can be selectively removed to provide a non-pressure bearing area to the foot.

In U.S. Pat. No. 5,762,622 a device is directed towards a medical boot with a unitary splint in which the splint element is positioned within an inflatable cushion insert.

SUMMARY OF THE INVENTION

A heel and foot plantar surface suspension device for use with orthopedic foot and ankle braces and the like. The foot surface suspension device comprises an elongated suspension pad that is positioned within a foot engagement enclosure to selectively support the foot allowing either the forefoot or heel plantar surface to be suspended therefrom without surface contact. The present invention has contoured portions that are selectively positioned to provide the desired suspension. Attachment surface and multiple extension straps are supplied to selectively position and secure the foot surface suspension device within the enclosure.

DESCRIPTION OF THE PREFERRED EMBODIMENT

Figure 1:
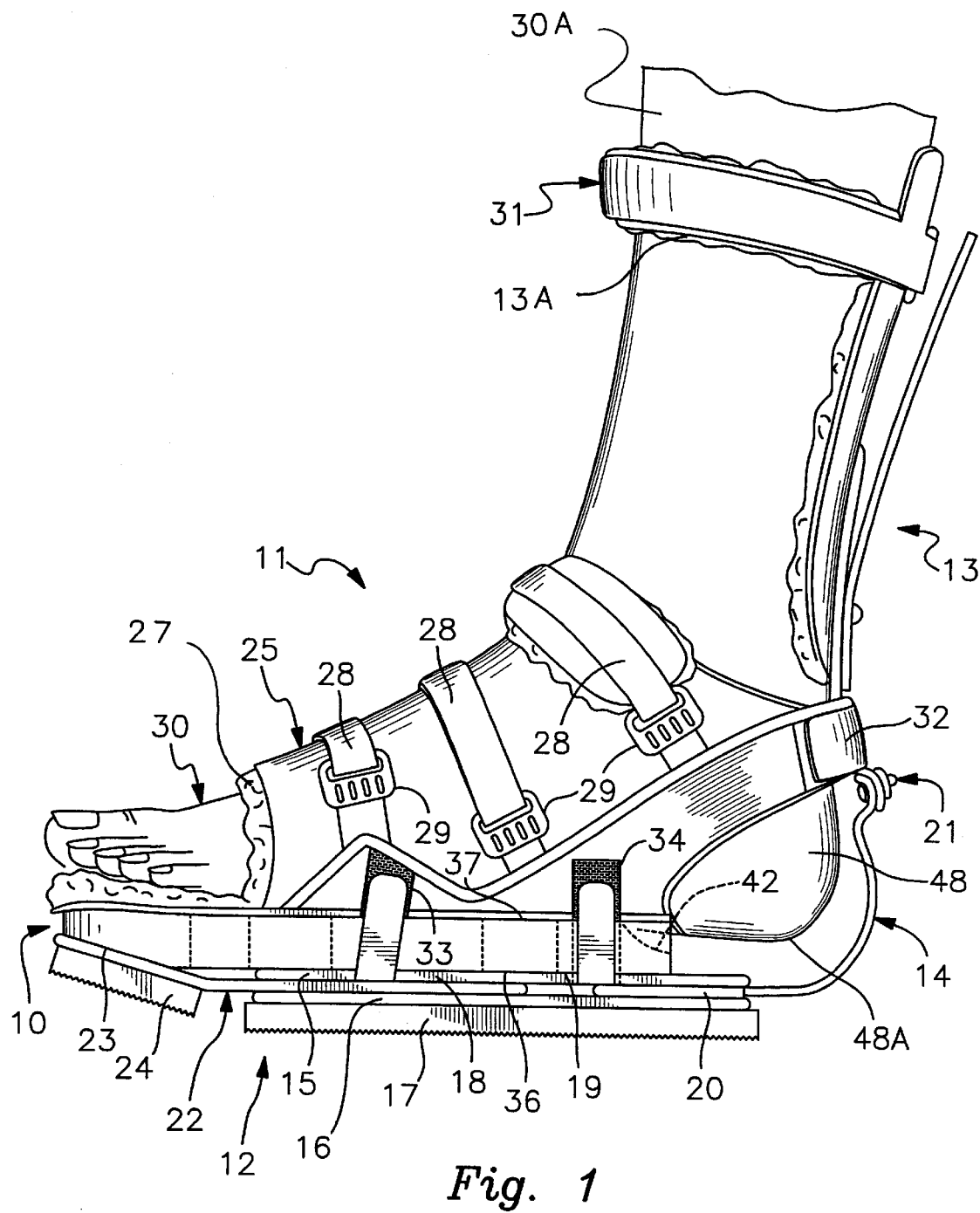
FIG. 1 is a side elevational view of the foot surface suspension device within an orthopedic foot brace suspending the heel portion of the foot.
Figure 2:
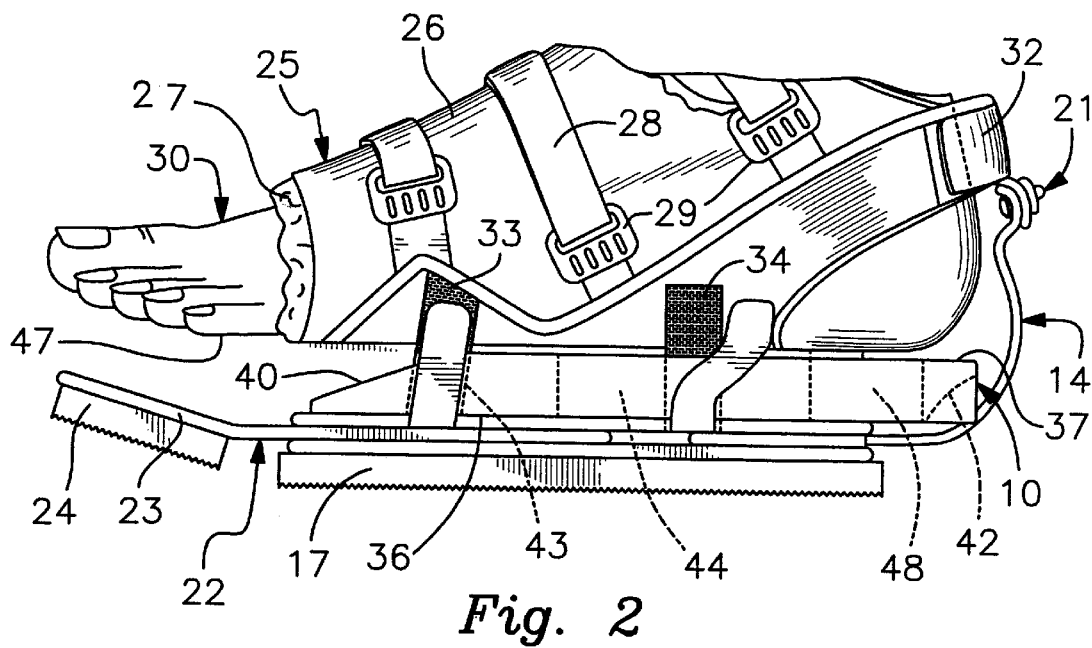
FIG. 2 is a partial side elevational view of a repositioned foot surface suspension device in an orthopedic foot brace in which the forefoot is suspended thereby.
Figure 3:
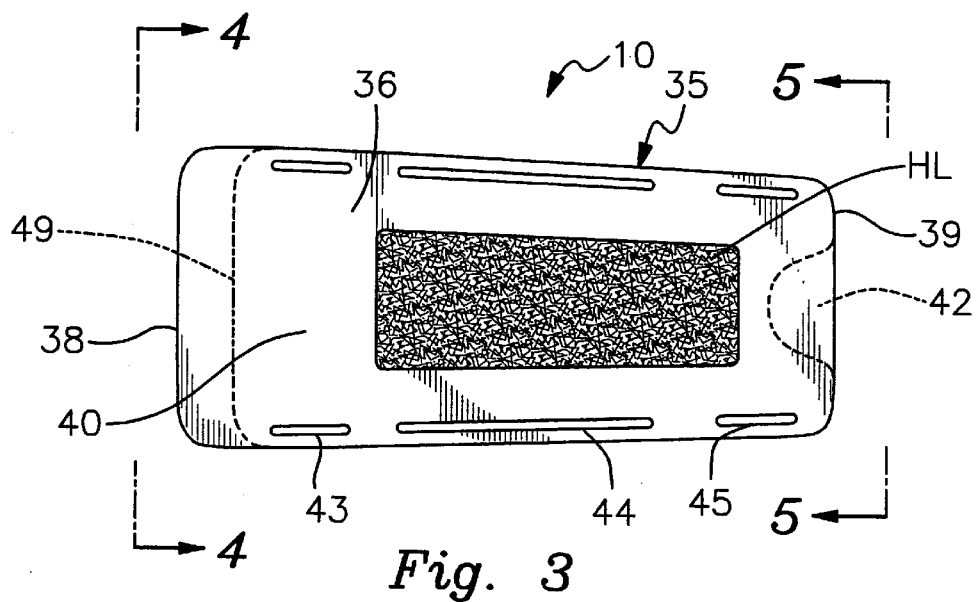
FIG. 3 is a top plan view of the foot surface suspension device of the invention.
Figure 4:
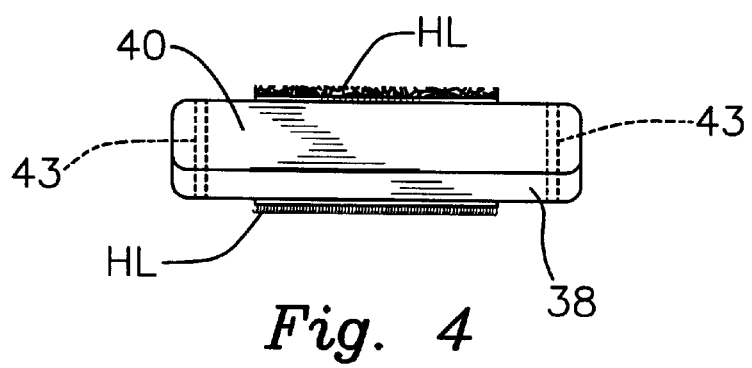
FIG. 4 is a front elevational view on lines 4—4 of FIG. 3.
Figure 5:
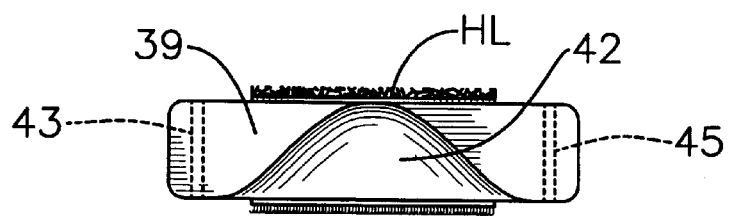
FIG. 5 is a rear elevational view on lines 5—5 of FIG. 3.
Figure 8:
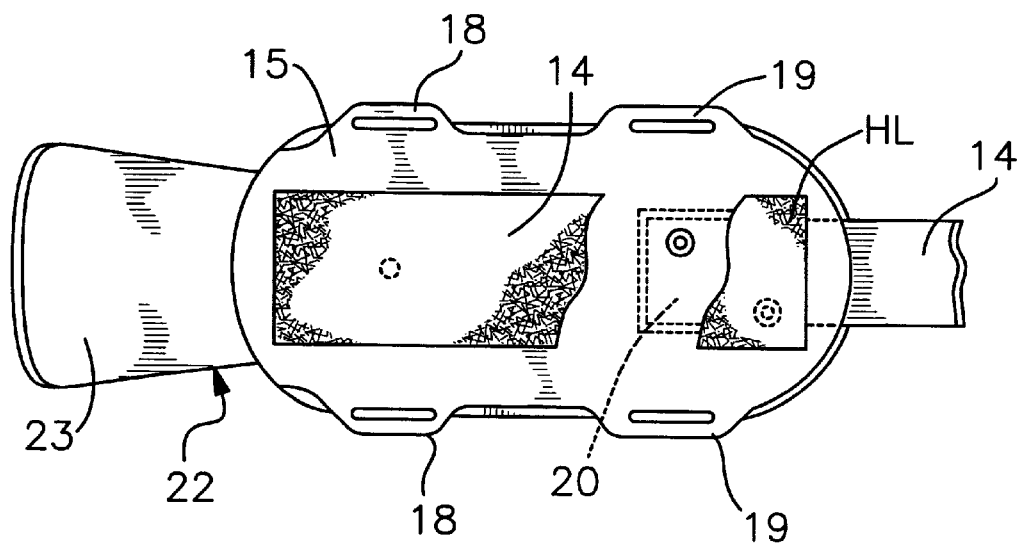
FIG. 8 is a top plan view of a sole engagement and attachment portion of an orthopedic brace with portions broken away.
Figures 9, 10:
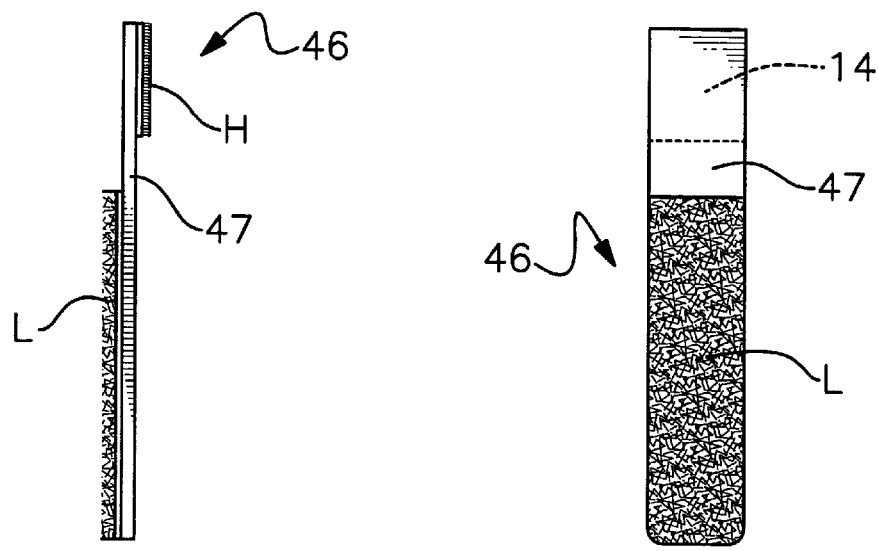
FIG. 9 is an enlarged side elevational view of an extension attachment strap for use with the foot surface suspension device.
FIG. 10 is an enlarged front elevational view of the extension strap illustrated in FIG. 4.

Referring to FIGS. 1, 2 and 8 of the drawings, the pressure relief insert 10 of the invention can be seen positioned within an orthopedic foot and ankle brace 11. The insert 10 has a foot portion 12, a leg portion 13 and an interconnecting heel portion 14 therebetween. The foot portion 12 has a footpad 15 secured to an attachment brace 16. A resilient walking pad 17 is secured to the base 16. The foot pad 15 is of a generally rectangular configuration with oppositely disposed longitudinally spaced apertured attachment tab pairs 18 and 19 extending therefrom, as best seen in FIG. 8 of the drawings. A mounting pocket 20 extends inwardly from the bottom of the footpad 15 for registerable engagement with the inner connecting heel portion 14 between the attachment brace 16 and the foot portion 15 by fasteners F. A compound adjustable hinge assembly 21 is positioned on the interconnecting heel portion 14 between the foot portion 12 and leg portion 13 and is described in greater detail by reference in applicant's U.S. Pat. No. 5,944,679.

A toe extension member 22 is adjustably secured to the under side of the footpad 15 by fasteners F opposite said mounting pocket 20 having an upturned angular offset end portion 23. A resilient toe pad 24 is secured to the underside of the end portion 23. A fabric foot enclosure 25 has a fabric sleeve 26 lined with a soft synthetic fur-like material 27. The fabric sleeve 26 has a plurality of longitudinally spaced enclosure straps 28 and correspondingly registering buckle assemblies 29 secured thereto that extend transversely over the sleeve 26 to secure the patient's foot 30 within. A leg strap and buckle assembly 31 extends from the leg portion 13 that has a fabric insert 13A around the patient's leg 30A as will be well understood by those skilled in the art.

The fabric sleeve 26 has a pair of interengaging heel strap extension members 32 that extend in overlapping relationship about a portion of the heel interconnecting member 14 and leg portion 13 respectively, as best seen in FIG. 1 of the drawings. Pairs of oppositely disposed attachment straps 33 and 34 extend in longitudinally spaced relation to one another from the fabric sleeve 26 for securing the sleeve to the foot portion 15.

Referring now to FIGS. 3–7 of the drawings, the pressure relief insert 10 of the invention can be seen having a generally rectangular body member 35 formed of a synthetic resin foam material commonly known as "cloud EVA" that has a consistency that can be shaped with cutting and grinding tools. The body member 35 has upper and lower surfaces 36 and 37 respectively and oppositely disposed ends at 38 and 39. A tapered upper surface portion 40 extends inwardly from the end 38 and will be discussed in greater detail hereinafter.

Figure 6:
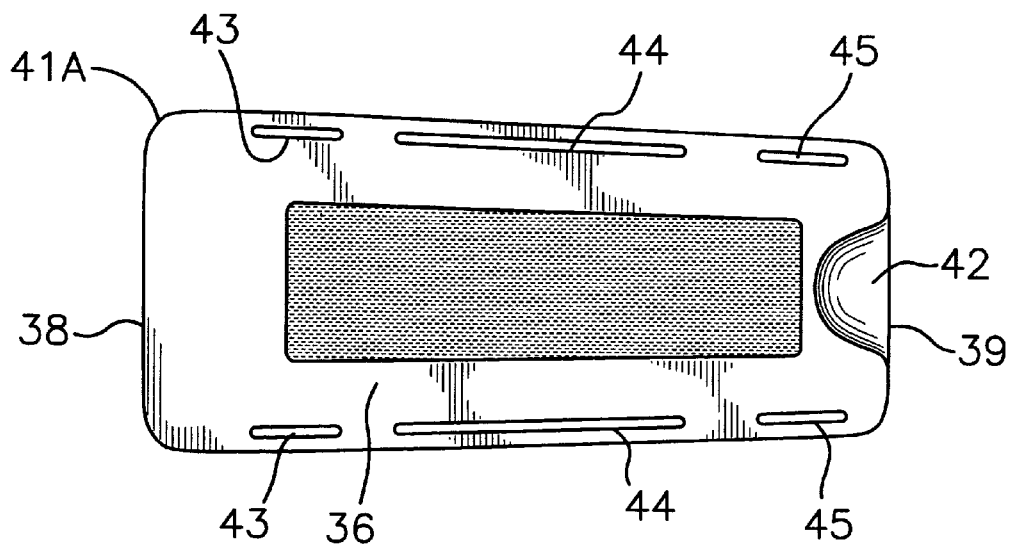
FIG. 6 is a bottom plan view of the foot surface suspension device.
Figure 7:
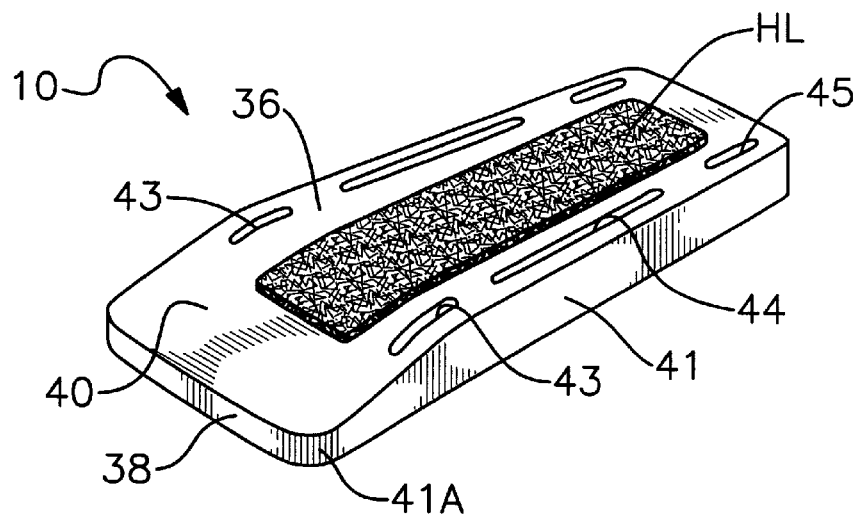
FIG. 7 is a perspective front, top and side view of the foot suspension surface device.

Oppositely disposed vertical sides 41 extend from the tapered surface portion 40 angularly inwardly towards one another to the body member's end 39. The intersection of the end 38 and the respective sides 41 are curved at 41A as best seen in FIGS. 6 and 7 of the drawings. A contoured recess area 42 extends inwardly in the bottom surface 37 from the end 39 midway between said respective sides 41. A plurality of longitudinally spaced paired parallel mounting slots 43, 44 and 45 extend through the body member 34 adjacent its respective sides 41. The mounting slots will be selectively aligned between the attachment strap pairs 33 and 34 and the respective apertured tab pairs 18 and 19 on the foot pad 15 as hereinbefore described.

In use, the pressure relief insert 10 is adjustably and releasably secured on the foot pad 15 by hook and loop material HL positioned on its respective upper and lower surfaces 36 and 37 and correspondingly on the opposing fabric sleeve 26 and foot portion 15 as best seen in FIGS. 1, 6 and 7 of the drawings.

Figure 11:
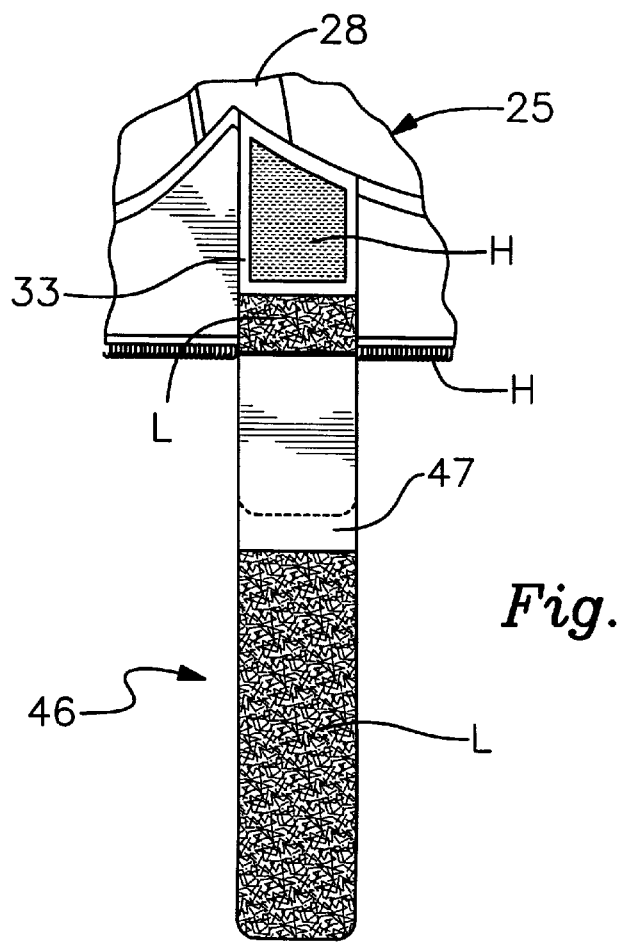
FIG. 11 is a front elevational view of an extension strap mounted on a portion of the orthopedic foot brace with the surface foot suspension device of the invention in place.

Referring now to FIGS. 1, 2 and 9–11 of the drawings, multiple mounting strap extensions 46 can be seen each having a fabric base 47 with a select section of hook fastening material H on its surface extending inwardly from one end thereof. An elongated section of loop fastening material L on its opposing surface extends inwardly from the oppositely disposed end thereof. The strap extensions 46 are removably secured to the respective mounting strap pairs 33 and 34 that extend from the fabric sleeve 26 as seen in FIG. 11 of the drawings. The strap extensions 46 provide additional length needed to pass through their respective aligned slots 43, 44, and 45.

Referring now to FIG. 1 of the drawings, the pressure relief insert 10 is shown within the orthopedic foot and ankle brace 11 with its upper surface 36 inverted and selectively secured against the foot portion 15. The pressure relief insert 10 is positioned forward so as to overlie the toe extension portion 23 being accommodated by the hereinbefore-described tapered surface 40. The strap extensions 46 therefore extend through the respective slot pairs 44 and 45, through the apertured tabs 18 and 19 and back upon themselves by inner engagement of the respective hook and loop materials thereon as will be well understood by those skilled in the art.

The patient's heel 48 is centered and stabilized by the recessed area 42 with the heel's plantar surface 48A suspended from contact with the foot portion 15.

The second mounting position of the pressure relief insert 10 is illustrated in FIG. 2 of the drawings in which the pressure relief insert 10 is inverted from that in FIG. 1 and repositioned for direct engagement with the heel's plantar surface 48A. In this configuration the mounting strap extensions 46 extend through respective aligned slot pairs 43 and 44, through the apertured tab pairs 18 and 19 and back upon themselves as hereinbefore described. In this position the tapered portion 40 of the upper surface 36 provides additional clearance for the patient's forefoot plantar surface 47 suspending same above the toe extension member 22. The pressure relief insert 10 is of a dimensional characteristic that it can be foreshortened by removing a portion of its tapered end surface 40 as indicated by broken lines at 49 in FIG. 3 of the drawings. This will allow for adjustable use requirements as determined by the patient's foot size without interfering with the dual suspension nature of the insert 10, as noted above.

It will also be evident from the above description that the pressure relief insert 10 of the invention due to the nature of its composite synthetic resin material preferably used in this construction, that it can easily be reshaped to increase specific forefoot and heel plantar surface suspension requirements afforded thereby.

It will be seen that a new and novel pressure relief insert has been illustrated and described and it will be apparent to those skilled in the art that various changes and modifications may be made therein without departing from the spirit of the invention.

Therefore We claim:

1. A pressure relief insert for therapeutic foot enclosures comprises,
    an elongated suspension pad positioned within the therapeutic foot enclosure for engagement by a foot,
    the suspension pad having selective upper and lower foot engagement surfaces and selective oppositely disposed foot enclosure engagement surfaces,
    a tapered forefoot surface on said upper foot engagement surface extending from one end thereof,
    a contoured recessed plantar heel alignment area in said oppositely disposed lower foot engagement surface in oppositely disposed relation to said tapered forefoot surface inwardly from the remaining end thereof,
    a plurality of slots extending through said suspension pad in spaced parallel longitudinal alignment adjacent respective longitudinal sides of said suspension pad,
    a plurality of fastener extension strips extending through said respective aligned slots and said therapeutic foot enclosure,
    areas of selected fastening material on oppositely disposed surfaces of said suspension pad for selective registerable engagement with corresponding fastening material on said foot enclosure.

2. The pressure relief insert set forth in claim 1 wherein said suspension pad has a first heel suspension position and a second forefoot suspension position.

3. The suspension pad set forth in claim 2 wherein said first heel suspension position comprises, the tapered forefoot engagement surface engageable on said therapeutic foot enclosure and the contoured recess area engageable on a portion of said heel for suspension of the plantar heel portion of said foot therefrom.

4. The suspension pad set forth in claim 2 wherein said second forefoot suspension portion comprises the selected upper foot engagement surface opposite of said contoured recessed area engageable by said plantar heel portion suspending said plantar forefoot portion in relation to said foot pad.

5. The pressure relief insert set forth in claim 1 wherein said contoured recess area is midway between said respective longitudinal sides.

6. The pressure relief insert set forth in claim 1 wherein said suspension pad is preferably made of synthetic resin foam material.

7. The pressure relief insert set forth in claim 1 wherein said respective longitudinal sides of said suspension pad are inclined towards one another from the tapered forefoot surface area.

8. A pressure relief insert for therapeutic foot devices comprises, an elongated suspension pad having oppositely disposed ends, with spaced opposing sides extending therebetween,
    a tapered surface portion extending inwardly from one of said ends,
    an oppositely disposed opposing contoured recess area extending inwardly from said remaining end midway between said respective sides,
    said suspension pad selectively positioned in a first position in said therapeutic foot device engageable with a plantar heel portion of a human foot opposite said contoured recess area suspending the plantar forefoot portion therefrom, said suspension pad positioned in
    a second position in said therapeutic device for engagement with a plantar forefoot portion of the foot opposite said tapered surface suspending the plantar heel portion of the foot,
    a plurality of slots within said suspension pad in spaced paired parallel relation adjacent said respective sides,
    fastening elements extending through said slots for engagement with respective foot devices,
    secondary fastening elements on oppositely disposed engagement surfaces of said suspension pad.

9. The pressure relief insert set forth in claim 8 wherein said suspension pad is made of synthetic resin foam material.

10. The pressure relief insert set forth in claim 8 wherein said fastening elements extending through said slots in said suspension pad comprises, strap extensions having hook and loop fastening material on respective oppositely disposed end sides thereof.

11. The pressure relief insert set forth in claim 8 wherein said secondary fastening elements on said opposing surfaces of the suspension pad are of alternating hook and loop material for registration with corresponding hook and loop engagement material on said opposing surfaces of said foot device.

* * * * *